(12) United States Patent
Svoboda et al.

(10) Patent No.: US 6,462,562 B1
(45) Date of Patent: Oct. 8, 2002

(54) DIFFERENTIAL CAPACITANCE PROBE FOR PROCESS CONTROL INVOLVING AQUEOUS DIELECTRIC FLUIDS

(75) Inventors: John M. Svoboda, Idaho Falls, ID (US); John L. Morrison, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/723,541

(22) Filed: Nov. 28, 2000

(51) Int. Cl.[7] .............................................. G01R 27/26
(52) U.S. Cl. ........................ 324/663; 324/664; 324/665
(58) Field of Search ................................. 324/663, 664, 324/665, 694, 698; 73/32 R, 304 C

(56) References Cited

U.S. PATENT DOCUMENTS

| | | | |
|---|---|---|---|
| 3,768,006 A | * 10/1973 | Mueller | 324/665 |
| 3,988,668 A | 10/1976 | Bowers | 324/61 P |
| 4,011,746 A | * 3/1977 | Weitz, Jr. et al. | 324/685 X |
| 4,882,648 A | 11/1989 | Verrando, III | 361/286 |
| 4,935,215 A | * 6/1990 | Krishnamurthy | 423/328 |
| 5,125,265 A | 6/1992 | O'Connell et al. | 73/61.41 |
| 5,142,909 A | 9/1992 | Baughman | 73/304 C |
| 5,260,667 A | * 11/1993 | Garcia-Golding et al. | 324/694 |
| 5,436,565 A | 7/1995 | Gammell | 324/679 |
| 5,861,755 A | 1/1999 | Moerk et al. | 324/663 |

* cited by examiner

*Primary Examiner*—N. Le
*Assistant Examiner*—T. R. Sundaram
(74) *Attorney, Agent, or Firm*—Thorpe North & Western

(57) ABSTRACT

A differential capacitance probe device for process control involving aqueous dielectric fluids is disclosed. The device contains a pair of matched capacitor probes configured in parallel, one immersed in a sealed container of reference fluid, and the other immersed in the process fluid. The sealed container holding the reference fluid is also immersed in the process fluid, hence both probes are operated at the same temperature. Signal conditioning measures the difference in capacitance between the reference probe and the process probe. The resulting signal is a control error signal that can be used to control the process.

18 Claims, 2 Drawing Sheets

DIFFERENTIAL CAPACITANCE PROBE FOR PROCESS CONTROL INVOLVING AQUEOUS DIELECTRIC FLUIDS

CONTRACTUAL ORIGIN OF THE INVENTION

This invention was made with United States Government support under Contract No. DE-AC07-94ID13223, now Contract No. DE-AC07-99ID13727 awarded by The United States Government has certain rights in this invention.

BACKGROUND OF THE INVENTION

This invention relates to a differential capacitance probe. More particularly, the invention relates to a differential capacitance probe that detects small differences in complex dielectric constant of a process fluid as compared to a reference fluid. This differential capacitance probe yields a control error signal in real time such that the process can be controlled.

A problem that is frequently encountered in certain industrial processes is how to measure very small differences in complex dielectric constant where such differences are indicative of a critical parameter of a process that is to be controlled The relative dielectric constant, $\epsilon_r$, of water is approximately 80, and many critical aqueous processes will vary the $\epsilon_r$ of water by a small fraction. Direct measurement of a small change in $\epsilon_r$, in the presence of other parameter sensitivities such as temperature coefficients, is very difficult. For many process control applications, however, the direct measurement of $\epsilon_r$ is not necessary. What is needed is an error signal that indicates to a process controller that the process $\epsilon_r$ is either above or below the desired $\epsilon_r$ and, as corrections are made, that the sign and magnitude of the error signal measures the quality of the correction.

In view of the foregoing, it will be appreciated that providing a differential capacitance probe that provides an error signal in real time, thus enabling correction of a critical parameter of the process, would be a significant advancement in the art.

BRIEF SUMMARY OF THE INVENTION

It is an object of the present invention to provide a differential capacitance probe that enables real time control of process operations involving aqueous solutions of organics wherein the process variable is a very small percent by weight of the solution.

It is also an object of the invention to provide a differential capacitance probe having a reference probe and a process probe both operated at the same temperature.

It is another object of the invention to provide a differential capacitance probe that yields an output that is a control error signal that can be used to control the process.

It is still another object of the invention to provide a differential capacitance probe that uses a pair of matched capacitance probes, one immersed in a sealed container of a reference fluid, and the other immersed in the process fluid.

It is yet another object of the invention to provide a differential capacitance probe that is suitable for use in industries such as food processing and paper mill operations.

It is a further object of the invention to provide a differential capacitance probe that does not generate hazardous waste.

These and other objects can be addressed by providing a system for controlling a process including a process aqueous dielectric fluid having at least one variable parameter, the system comprising:

(a) a first probe configured for being immersed in the process aqueous dielectric fluid, the first probe configured for measuring at least the capacitance of the process aqueous dielectric fluid; and (b) a second probe configured for being immersed in a reference dielectric fluid wherein the reference dielectric fluid is isolated from the process aqueous dielectric fluid, the second probe configured for measuring at least the capacitance of the reference aqueous dielectric fluid;

(c) a power source, the first probe and the second probe being connected to the power source such that the current provided to the first probe and the second probe is directly proportional and the first probe generates a first measurement signal and the second probe generates a second measurement signal;

(d) means for detecting the difference between the first measurement signal and the second measurement signal and outputting an error signal, the error signal being used to promotionally alter the variable parameter to modify the process aqueous dielectric fluid.

In a preferred embodiment of this system, the second probe and reference dielectric fluid are sealed in a temperature-permeable container. Preferably, the first probe and the second probe are coupled in-parallel to the power source and the first probe and the second probe each comprise spaced apart plates having the same surface areas and distance between the plates. It is also preferred that the first measurement signal and the second measurement signal comprise current signals, and that the means for detecting differences between the current signals comprises an amplifier.

Another preferred embodiment of the invention relates to an apparatus for producing an error signal when a complex dielectric constant of a process aqueous dielectric fluid differs from a complex dielectric constant of a reference dielectric fluid comprising:

(a) a power source;

(b) a differential capacitance probe coupled to the power source comprising:
  (i) a first capacitor probe configured for being immersed in the process aqueous dielectric fluid, and
  (ii) a second capacitor probe configured for being immersed in the reference dielectric fluid and isolated from the process aqueous dielectric fluid,
  wherein the first capacitor probe and the second capacitor probe are configured in parallel, the first capacitor probe is configured for generating a first current measurement signal, and the second capacitor probe is configured for generating a second current measurement signal;

(c) a device coupled to the differential capacitance probe for receiving the first current measurement signal and the second current measurement signal and producing an error signal when the first current measurement signal differs from the second current measurement signal.

Still another preferred embodiment of the invention comprises a method for producing an error signal when a complex dielectric constant of a process aqueous dielectric fluid differs from a complex dielectric constant of a reference dielectric fluid comprising:

(a) in connection with a system for controlling a process including the process aqueous dielectric fluid having at least one variable parameter, the system comprising:
  (i) a first probe configured for being immersed in the process aqueous dielectric fluid, the first probe configured for measuring at least the capacitance of the process aqueous dielectric fluid, (ii) a second probe configured for being immersed in the reference dielectric fluid wherein the reference dielectric fluid is isolated from the process aqueous dielectric fluid, the second probe configured for measuring at least the capacitance of the reference dielectric fluid, (iii) a power source, the first probe and the second probe being connected to the power source such that the current provided to the first probe and the second probe is directly proportional and the first probe generates a first measurement signal and the second probe generates a second measurement signal;

(iv) means for detecting the difference between the first measurement signal and the second measurement signal and outputting an error signal, the error signal being used to promotionally alter the variable parameter to modify the process aqueous dielectric fluid, immersing the second probe in the isolated reference dielectric fluid;

(b) immersing the first probe and the isolated second dielectric fluid, having the second probe immersed therein, in the process aqueous dielectric fluid;

(c) causing the power source to provide current to the first probe and the second probe such that the first probe generates the first measurement signal and the second probe generates the second measurement signal such that the means for detecting thereby outputs the error signal when the dielectric constant of the process aqueous dielectric fluid differs from the dielectric constant of the reference dielectric fluid.

DETAILED DESCRIPTION

Before the present differential capacitance probe is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "an aqueous dielectric fluid" includes reference to two or more of such aqueous dielectric fluids, reference to "a measurement signal" includes reference to one or more of such measurement signals, and reference to "a parameter" includes reference to two or more of such parameters.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

Figure 1:
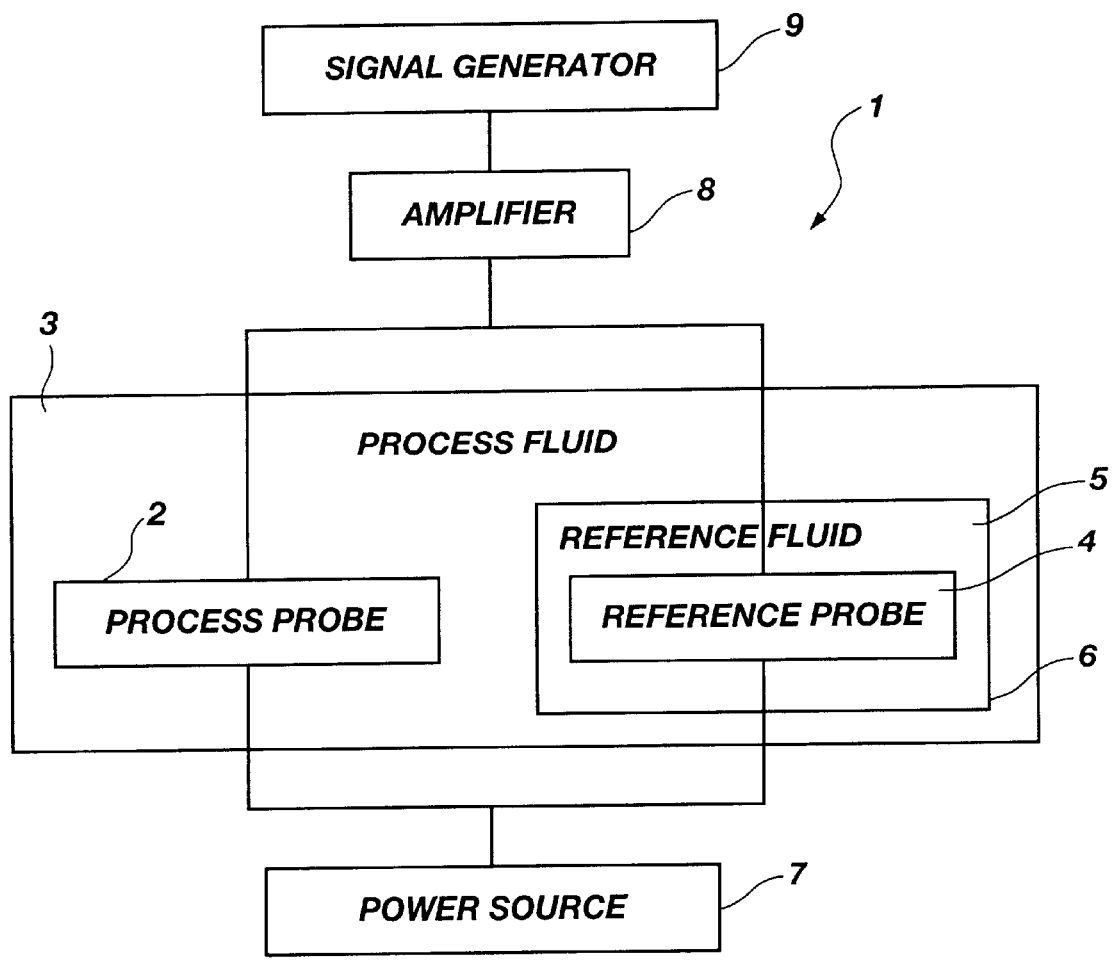
FIG. 1 shows a block diagram of a differential capacitance probe according to the present invention.

FIG. 1 shows a block diagram of an illustrative differential capacitance probe according to the present invention. In FIG. 1 there is illustrated a system 1 for controlling a process that includes an aqueous dielectric fluid. This aqueous dielectric fluid may include a complex mixture of ingredients, such as a fluid that would be involved in paper making, food processing, or the like. This aqueous dielectric fluid has at least one variable parameter that requires tight control for optimum efficiency of the process, or perhaps even for successful operation of the process. This variable parameter could be, for example, concentration of an ingredient of the aqueous dielectric fluid that cannot be conveniently monitored in an inexpensive or timely fashion, but can be monitored by real time determination of the complex dielectric constant of the fluid. The system 1 comprises a process probe 2 configured for being immersed in the process aqueous dielectric fluid 3. This process probe 2 measures at least the capacitance of the process aqueous dielectric fluid. In a preferred embodiment of the invention, this process probe comprises spaced-apart plates, such as a conventional capacitor. The system 1 further comprises a reference probe 4, which is immersed in a reference aqueous dielectric fluid 5. The reference probe 4 and the reference aqueous dielectric fluid 5 are isolated from the process aqueous dielectric fluid 3, such as by being sealed in a container 6. Preferably, such a container 6 is temperature-permeable, and the container 6 is immersed in the process aqueous dielectric fluid 3. This permits, after equilibration, temperature differences between the process aqueous dielectric fluid and the reference aqueous dielectric fluid to be canceled out as a source of differences in complex dielectric constant between the two fluids. Both the process probe 2 and the reference probe 4 are coupled in parallel to a power source 7 such that each probe generates a measurement signal. Preferably, this measurement signal is a current measurement. The process probe 2 and the reference probe 4 are also coupled to a device 8 for detecting the difference between the first measurement signal and the second measurement signal, such as an amplifier. The device is, in turn, coupled to a signal generator 9 for generating an error signal when the two measurement signals are different. This error signal is generated in real time and indicates that the variable parameter needs to be altered for modifying the process aqueous dielectric fluid.

With an understanding of the major functions carried out by the preferred embodiments of the present invention, a further description of one preferred embodiment of the present invention will be provided. It is to be understood that the following description is merely one example of the structures which can be used to carry out the present invention.

Figure 2:
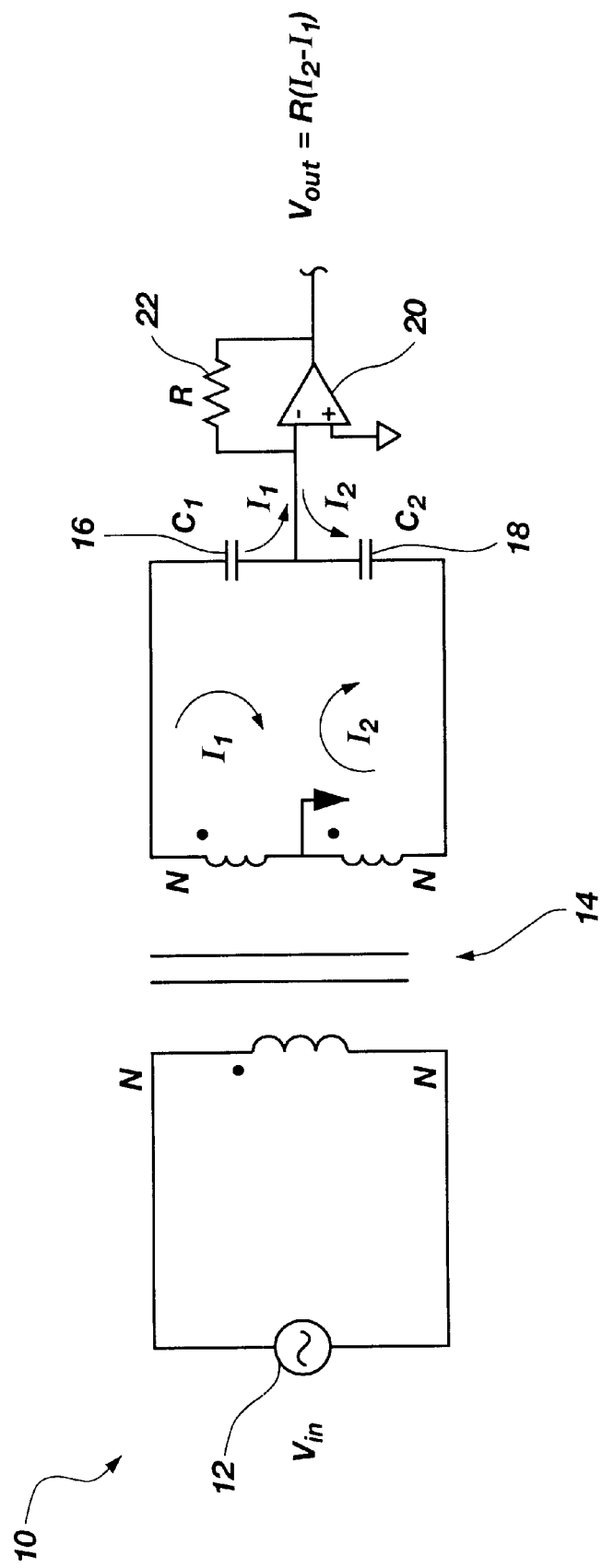
FIG. 2 shows an illustrative circuit diagram of a differential capacitance probe according to the present invention.

One preferred embodiment of the present invention comprises two matched capacitance probes, i.e. a reference capacitance probe and a process capacitance probe, as shown in FIG. 2. The reference capacitance probe is immersed in a sample of a reference aqueous solution (i.e., process fluid having a selected dielectric constant), and the reference capacitance probe and the sample of reference aqueous solution are both preferably hermetically sealed in a temperature-permeable container. The process capacitance probe is preferably disposed on the outside of the sealed container. The process capacitance probe and the reference capacitance probe are sealed in its container are then immersed in the process fluid that is to be assayed such that the process capacitance probe comes in contact with the process fluid. Each of the capacitance probes produces a signal, and the difference between the two signals is the desired process control error signal. That is, the difference between the two signals indicates the difference between the dielectric constant of the process fluid and the dielectric constant of the reference fluid. The temperature conditions for the two capacitance probes are the same, since both probes are immersed in the process fluid. Thus, the effects of temperature are negligible, as the temperature will only affect the magnitude of the error and not the sign. Therefore, the process controller could, in the presence of temperature variations, regulate that error to zero.

The following simple relations define the measurement signal. If the same voltage source drives both parallel halves of the differential capacitance probe and the output is the current difference between the probes:

$$I_1 - I_2 = V_{IN}\left(jw(C_1 - C_2) + \left(\frac{1}{R_1} - \frac{1}{R_2}\right)\right)$$

wherein $I_1$ represents the current from the process capacitance probe, $I_2$ represents the current from the reference capacitance probe, $V_{IN}$ represents the voltage into the circuit, j represents the square root of –1, w represents radian frequency, $C_1$ represents the capacitance of the process dielectric, $C_2$ represents the capacitance of the reference dielectric, $R_1$ represents the resistance present in the current path through the process dielectric fluid, and $R_2$ represents the resistance present in the current path through the reference dielectric fluid. Thus, the differential capacitance is:

$$C_1 - C_2 = \frac{I_M(I_1 - I_2)}{wV_{IN}}$$

wherein $C_1$, $C_2$, $I_1$, $I_2$, and $V_{IN}$, and w are as defined above, and $I_M$ represents imaginary part of the difference between currents $I_1$ and $I_2$, divided by $wV_{IN}$; and the differential conductance is:

$$\left(\frac{1}{R_1} - \frac{1}{R_2}\right) = \frac{R_E(I_1 - I_2)}{V_{IN}}$$

wherein $R_1$, $R_2$, $I_1$, $I_2$, and $V_{IN}$ are as defined above and $R_E$ represents the real part of the difference between currents $I_1$ and $I_2$, divided by $wV_{IN}$. Therefore, the differential dielectric constant is:

$$\varepsilon'_1 - \varepsilon'_2 = \frac{d}{A}(C_1 - C_2)$$

wherein d, A, $C_1$, and $C_2$ are as defined above, $\varepsilon'_1$ represents the dielectric constant of the process dielectric, and $\varepsilon'_2$ represents the dielectric constant of the reference dielectric, and the differential conductivity is:

$$\sigma_1 - \sigma_2 = \frac{d}{A}\left(\frac{1}{R_1} - \frac{1}{R_2}\right)$$

wherein d, A, $R_1$, and $R_2$ are as defined above, $\sigma_1$ represents the conductivity of the process dielectric, and $\sigma_2$ represents the conductivity of the reference dielectric.

FIG. 2 illustrates the equivalent circuit. The circuit 10 comprises an alternating current source 12, which produces a voltage into the circuit ($V_{IN}$). A transformer 14 is used to build up or step down the voltage or current, as appropriate. The transformer is coupled to two parallel capacitor probes, a process capacitor probe 16 and a reference capacitor probe 18. These two capacitor probes are matched such that the plates comprising the capacitor probes have equal surface areas (A) and are separated by an equal distance (d). Each capacitor probe has an output current, $I_1$ and $I_2$, respectively, which feeds into an amplifier 20 coupled in parallel to a resistor 22. If the dielectric constants of the respective dielectric fluids into which the process capacitor probe 16 and the reference capacitor probe 18 are equivalent, then there is no output voltage from the amplifier. Such a condition is a signal that the process fluid needs no adjustment or correction. If, however, the dielectric constants of the dielectric fluids are not equivalent, then there is an output voltage from the amplifier, which functions as an error signal that the process fluid needs adjustment or correction upstream.

We claim:

1. A system for controlling a process including a process aqueous dielectric fluid having at least one variable parameter, the system comprising:

a first probe configured for being immersed in a process aqueous dielectric fluid, the first probe configured for measuring at least the capacitance of the process aqueous dielectric fluid;

a second probe configured for being immersed in a reference dielectric fluid that is in thermal communication with the process aqueous dielectric fluid and wherein the reference dielectric fluid is electrically and fluidly isolated from the process aqueous dielectric fluid, the second probe configured for measuring at least the capacitance of the reference aqueous dielectric fluid;

a power source, the first probe and the second probe being connected to the power source such that the current provided to the first probe and the second probe is directly proportional and the first probe generates a first measurement signal and the second probe generates a second measurement signal; and a device for detecting the difference between the first measurement signal and the second measurement signal and outputting at least one error signal;

a process controller for altering the at least one variable parameter to modify the process aqueous dielectric fluid upon the process controller receiving the at least one error signal.

2. The system of claim 1 further comprising a temperature-permeable container for isolating the second probe and reference dielectric fluid from the process aqueous dielectric fluid.

3. The system of claim 1 wherein the first probe and the second probe are coupled in parallel to the power source.

4. The system of claim 3 wherein the first probe and the second probe each comprise spaced apart plates having the same surface areas and distance between the plates.

5. The system of claim 1 wherein the first measurement signal and the second measurement signal are current signals.

6. The system of claim 1 wherein the power source is an alternating current source.

7. The system of claim 1 wherein the device for detecting comprises an amplifier.

8. Apparatus for producing an error signal useable by a process controller when a complex dielectric constant of a process aqueous dielectric fluid differs from a complex dielectric constant of a reference dielectric fluid, the apparatus comprising:
 a power source;
 a differential capacitance probe coupled to the power source comprising:
  a first capacitor probe configured for being immersed in a process aqueous dielectric fluid,
  a second capacitor probe configured for being immersed in the reference dielectric fluid electrically and fluidly isolated from the process aqueous dielectric fluid,
  wherein the first capacitor probe and the second capacitor probe are coupled in parallel, the first capacitor probe is configured for generating a first current measurement signal, and the second capacitor probe is configured for generating a second current measurement signal; and
 a device coupled to the differential capacitance probe for receiving the first current measurement signal and the second current measurement signal and producing an error signal useable by at least a process controller to alter at least one characteristic of the process aqueous dielectric fluid measurable by the first capacitor probe when the first current measurement signal differs from the second current measurement signal.

9. The apparatus of claim 8 further comprising a temperature-permeable container for electrically and fluidly isolating the second capacitor probe and a reference dielectric fluid from a process aqueous dielectric fluid.

10. The apparatus of claim 8 wherein the device comprises an amplifier.

11. The apparatus of claim 8 wherein the first capacitor probe and the second capacitor probe comprise spaced apart plates having the same surface areas and distance between the plates.

12. The differential capacitance probe of claim 8 wherein said power source is an alternating current source.

13. Apparatus for controlling a process, the apparatus producing an error signal when a complex dielectric constant of a process aqueous dielectric fluid differs from a complex dielectric constant of a reference dielectric fluid, the apparatus comprising:
 an alternating current power source;
 a differential capacitance probe coupled to the power source comprising:
  a first capacitor probe configured for being immersed in a process aqueous dielectric fluid, and
  a second capacitor probe configured for being immersed in a reference dielectric fluid to be held in electrical and fluid isolation form a process aqueous dielectric fluid in a temperature-permeable container,
  wherein the first capacitor probe and the second capacitor probe are configured in parallel, the first capacitor probe is configured for generating a first current measurement signal, and the second capacitor probe is configured for generating a second current measurement signal,
  wherein the first capacitor probe and the second capacitor probe comprise spaced apart plates having the same surface areas and distances between the plates;
 an amplifier coupled to the differential capacitance probe for receiving the first current measurement signal and the second current measurement signal and producing an error signal when the first current measurement signal differs from the second current measurement signal; and
 a process controller in communication with the amplifier, process controller capable of altering at least one variable parameter to modify a process aqueous dielectric fluid upon the process controller receiving an error signal from the amplifier when the first current measurement signal differs from the second current measurement signal.

14. A method for producing an error signal useable by a process controller when a complex dielectric constant of a process aqueous dielectric fluid differs from a complex dielectric constant of a reference dielectric fluid comprising:
 in connection with a system for controlling a process including the process aqueous dielectric fluid having at least one variable parameter, the system comprising:
  a first probe configured for being immersed in the process aqueous dielectric fluid, the first probe configured for measuring at least the capacitance of the process aqueous dielectric fluid,
  a second probe configured for being immersed in the reference dielectric fluid wherein the reference dielectric fluid is isolated from the process aqueous dielectric fluid, the second probe configured for measuring at least the capacitance of the reference dielectric fluid,
  a power source, the first probe and the second probe being connected to the power source such that the current provided to the first probe and the second probe is directly proportional and the first probe generates a first measurement signal and the second probe generates a second measurement signal;
  a detector for detecting the difference between the first measurement signal and the second measurement signal and outputting an error signal, the error signal being used to alter the variable parameter to modify the process aqueous dielectric fluid,
 immersing the second probe in the isolated reference dielectric fluid;
 immersing the first probe and the isolated second dielectric fluid, having the second probe immersed therein, in the process aqueous dielectric fluid;
 causing the power source to provide current to the first probe and the second probe such that the first probe generates the first measurement signal and the second probe generates the second measurement signal, such that the detector thereby outputs the error signal to a process controller when the dielectric constant of the process aqueous dielectric fluid differs from the dielectric constant of the reference dielectric fluid.

15. The method of claim 14 wherein the detector for detecting comprises an amplifier.

16. The method of claim 14 wherein the first probe and the second probe each compose spaced apart plates having the same surface areas and distances between the plates.

17. The method of claim 14 wherein the power source comprises an alternating current source.

18. The method of claim 14 further comprising disposing the second probe and the reference dielectric fluid in a temperature-permeable container.

* * * * *